United States Patent [19]

Tocker

[11] 4,282,209
[45] Aug. 4, 1981

[54] PROCESS FOR PREPARING INSECTICIDAL COMPOSITIONS

[75] Inventor: Stanley Tocker, Wilmington, Del.

[73] Assignee: E. I. Du Pont de Nemours and Company, Wilmington, Del.

[21] Appl. No.: 92,331

[22] Filed: Nov. 8, 1979

Related U.S. Application Data

[63] Continuation-in-part of Ser. No. 892,396, Mar. 31, 1978, abandoned.

[51] Int. Cl.³ .............. A61K 31/78; A01N 33/24; A01N 37/00; A01N 47/10
[52] U.S. Cl. .............................. 424/81; 424/78; 424/83; 424/298; 424/300; 424/327; 525/6
[58] Field of Search .............. 424/78, 81, 83, 298, 424/300, 327

[56] References Cited

U.S. PATENT DOCUMENTS

| | | | |
|---|---|---|---|
| 3,400,093 | 9/1968 | Feinberg | 260/29.6 |
| 3,576,834 | 4/1971 | Buchanan | 260/453 |
| 3,769,417 | 10/1973 | Van Breen | 424/78 |
| 3,966,902 | 6/1976 | Chromecek | 424/81 |
| 4,007,258 | 2/1977 | Cohen et al. | 424/22 |

FOREIGN PATENT DOCUMENTS 786777 6/1968 Canada .
846785 7/1970 Canada .

OTHER PUBLICATIONS

Coppedge et al.; J. Econ. Ent., vol. 68 (4), (1975), pp. 508–510.
Blank; C. A., vol. 79, (1973) 14455v.

*Primary Examiner*—Allen J. Robinson

[57] ABSTRACT

The instant invention relates to a process for preparing novel insecticide-polymer particles. The process consists essentially of dissolving the insecticide, methomyl, and a polymer in a solvent in which both are soluble. The solution is then comingled with a non-solvent for both the polymer and the methomyl under high shear conditions. A particulate product is formed consisting of irregularly shaped particles having methomyl embedded in a polymer matrix. The irregularly shaped particles may be dispersed, e.g. in water, and sprayed readily into an area of insect infestation.

7 Claims, No Drawings

PROCESS FOR PREPARING INSECTICIDAL COMPOSITIONS

RELATED APPLICATIONS

This application is a continuation-in-part of my copending application U.S. Ser. No. 892,396, filed Mar. 31, 1978, now abandoned.

BACKGROUND OF THE INVENTION

It has been recognized that particles of insecticide may be used effectively to control insects while simultaneously controlling the speed of release of the insecticide and thus minimizing any undesirable effects. Traditionally, processes for preparing such particles have involved co-melting the pesticide with a barrier which may be a polymer. After the polymer and insecticide have been melted together, a grinding step takes place in which the particles are reduced to the desired size. This sort of technique is taught in Canadian Pat. No. 846,785 to G. C. Allen, in Coppedge et al., J. Economic Entomology 68, 508 (1976) and in Canadian Patent No. 787,777.

The co-melting technique is subject to disadvantages. For instance, one is limited with regard to the polymers which may be utilized because high melting or non-melting polymers are inoperable. Thus, a large number of polymers which may prove useful in a controlled release particle must, unfortunately, be eliminated from consideration. Another disadvantage stems from the fact that melting may deleteriously affect certain insecticides. Finally, this process necessitates a grinding step, an oftentimes difficult step which can adversely affect the structural integrity of the particles.

Other techniques which have been used to prepare insecticide particles include microencapsulation which tends to be quite expensive and which usually results in the presence of by-products in the insecticidal formulation itself. Other known methods require tedious control during production and have not always produced desirable particulate products. These methods are difficult to apply to methomyl because of the difficulty in matching the solubility characteristics of methomyl to the physical conditions required in these processes.

Thus, a need exists for a process for producing particles of insecticide, such as methomyl, embedded in a polymer. These particles should be efficiently and rapidly produced and should release the insecticide in a controlled fashion so that desired crops such as cotton are not injured. In addition, it is desired that the particles exhibit a combination of high initial and long residual insecticidal activity. This combination of characteristics are not readily found in available controlled release pesticide products.

SUMMARY OF THE INVENTION

According to the instant invention, a unique process has been found which unexpectedly produces particles which fulfill all of these requirements.

This new process involves the following steps. Initially, methomyl, known chemically as S-methyl-N-(methylcarbamoyl)oxythioacetamidate, and a polymer are dissolved in one or more organic liquids. The solution is then co-mingled by any conventional high shear method (e.g., stirring in a Waring blender) with a non-solvent or mixture of non-solvents for both methomyl and the polymer. Almost immediately, particles of polymer embedded with methomyl precipitate from the solution in particulate form. The resulting precipitate is washed with non-solvent to remove solvent and is then washed with water to remove unembedded or free methomyl. The particles are recovered and dried.

DETAILED DESCRIPTION OF THE INVENTION

The polymers which may be used in the process of this invention must be water-insoluble, have low permeability to water and must be capable of dissolving in an organic liquid which is also able to solubilize methomyl. The polymer should also have an inherent viscosity of at least about 0.2, measured for 0.25 g of polymer in 50 ml solvent at 20° C. using a No. 50 Cannon-Fenske viscometer. It is preferred that the polymer have an inherent viscosity between about 0.3 and 2.0, and more preferred that it have a viscosity above about 0.4.

As mentioned above, the polymer should have low water absorption, preferably in the range of 0.01 to 5.0% as measured by the ASTM test method D-570. The polymer must also be substantially soluble in an organic solvent; by this it is meant that least about 1.0% will dissolve in the solvent at room temperature. It is also preferable that the polymer have a softening point above ambient temperature so that the polymer may be stored without agglomeration.

The polymers which may be utilized and methods of preparing them are well-known in the art. The following polymers, with inherent viscosities of above about 0.2, may be used: acrylonitrile-butadienestyrene terpolymer (ABS), ABS modified polyvinyl chloride; ABS-polycarbonate blends; acrylic resins and copolymers such as poly(methacrylate; poly(ethylmethacrylate); methylmethacrylate or ethylmethacrylate copolymers with other unsaturated monomers; casein; cellulosic polymers such as ethyl cellulose, cellulose acetate, cellulose acetatebutyrate; epoxies, ethylene copolymers such as ethylene vinyl acetate-methacrylic acid and ethylene-acrylic acid copolymers; methylpentene polymers; modified phenylene oxides; polyamides; melamine formaldehydes; phenolformaldehydes; phenolic resins; polycarbonates; polyesters; polystyrene and its copolymers; urea-formaldehyde; urethanes; and vinyl resins such as vinyl chloride-vinyl acetate copolymers, polyvinyl chloride and poly(vinyl acetate).

Some polymers may require additional polymerization to give solid compositions. This can be done by the addition of heat and/or a catalyst in the processing or finishing step.

The invention also includes the use of mixtures of two or more of the above polymers in conjunction with methomyl.

The polymers which are preferred for this invention are the following: poly(methylmethacrylate), poly(ethylmethacrylate), ethyl cellulose, cellulose acetate, cellulose acetabutyrate, polystyrene, poly(vinyl)chloride and poly(vinylacetate).

Also preferred are copolymers of methyl methacrylate, ethyl methacrylate or styrene containing up to about 10% of at least one other polar comonomer. It is recognized in the art that the addition of small proportions of a monomer to a polymer does not change the basic characteristics of the polymer. Possible comonomers are other acrylates or methacrylates, acrylonitrile and styrene. Specific examples of useful copolymers are methyl methacrylate-ethyl methacrylate containing 5% ethyl methacrylate; methyl methacrylateethyl methacrylate-acrylonitrile terpolymer containing 6% ethyl methacrylate and 4% acrylonitrile; ethyl methacrylate-methyl acrylate copolymer containing 9% methylacrylate; and styrene-ethyl methacrylate copolymer containing 10% ethyl methacrylate. Other suitable copolymers would be obvious to one skilled in the art.

Still another type of polymer which is preferred is a vinyl chloride-vinyl acetate copolymer. Preferably, such a copolymer will contain up to about 20% vinyl acetate. An example of a suitable copolymer is a rigid vinyl cchloride-vinyl acetate copolymer containing 12% vinyl acetate as described in Schildknecht, "Vinyl and Related Polymers," p. 429, the disclosure of which is herein incorporated by reference.

The most preferred polymer, for reasons of efficiency and economy is poly(methylmethacrylate).

The solvent used must be an organic liquid capable of dissolving both the polymer and the methomyl or capable of dissolving the polymer and suspending the methomyl. The solvent must also be miscible with the non-solvent used in the process. Preferred solvents include halogenated aliphatics such as methylene chloride, methylene dichloride, ethylene dichloride, trichloroethylene, perchloroethylene and acetone.

The non-solvent is a liquid which does not solubilize either the polymer or methomyl. It must be miscible with the solvent used in the process. A wide range of non-solvents may be used; these would be readily discernible to one skilled in the art. Typically, the non-solvent is a hydrocarbon, and it is preferably an alkane of five to eight carbons or kerosene. When acetone is used as the solvent, cold water can be used as the non-solvent.

The concentration of methomyl present in the methomyl-polymer solution is preferably about 1–50% by weight. The amount of methomyl is more preferably 3–35% by weight and most preferably 5–20% by weight. The amount of polymer in the solution varies depending on the polymer and the solvent used and is generally dependent upon the solubility and viscosity of the polymer. Preferably, the polymer concentration is within the range of about 1–60 weight %, more preferably within the range of 10–50 weight % and most preferably in the range of 10–40 weight %.

The volume ratio of solvent to non-solvent is ideally within the range of 1 to 1 and 1 to about 100, preferably between about 1 to 2 and 1 to 10. One skilled in the art would easily be able to determine the optimum solvent and non-solvent ratios to use in connection with a given set of conditions.

The polymer-methomyl solution must be contacted with the non-solvent under high shear conditions in order to obtain a finely divided product. In a batch process, it is generally preferable to slowly add the polymer-methomyl solution to the agitated cooled non-solvent.

The agitation may be performed by any conventional high-shear blender such as those manufactured by Waring, Oster or a homo-mixer manufactured by Gifford-Wood. Other high shear blenders which may be used include colloid mills, jet mixers and the like. Typically, the high shear blending occurs above 1000 rpm.

The temperature of the non-solvent when comingled with the methomyl-polymer solution is preferably between 20° and −50° C. and more preferably between −10° and −30° C., depending on the freezing point of the non-solvent. The temperature of the methomyl-polymer solution is preferably between 15° and 35° C. If the temperature of the solution is too low, the solution's viscosity will be too high, and it will not be possible to spray or add the solution to the non-solvent in the form of small drops.

Various precipitation aids may be used. They include the following general modifications which are found to facilitate the formation of a finely divided product.

(a) use of a cooled non-solvent;

(b) use of a hydrocarbon soluble surfactant in the non-solvent to reduce or eliminate agglomeration;

(c) use of dilute solutions of methomyl and polymer; a limited amount of the non-solvent can be used expeditiously for this purpose where additional solvent is undesirable;

(d) pressure spraying of polymer methomyl solution in the form of finely divided droplets into the rapidly agitated non-solvent;

(e) use of continuous precipitation conditions that continuously expose the polymer solution to fresh precipitation non-solvent under high shear conditions; for example, having polymer and non-solvent streams meet in a tee or bullet mixer;

(f) use of the lowest molecular weight polymer consistent with the barrier characteristics; desired (generally, the higher molecular weight polymers are more resistant to permeation by water and extraction of methomyl); and (g) use of inert particulate materials such as silica or talc.

The precipitated particles containing polymer and embedded methomyl may be washed free of excess methomyl with non-solvent and water, if desired.

The resultant particulate product may be further reduced in size, if desired, by conventional milling procedures, for example, air, sand or ballmilling. Generally, it is best to wash with water after such a grinding step to remove freshly exposed methomyl.

The particles formed by this process are irregular in shape and tend to be under about 300 microns in size in their longest dimension. Typically, about 90% of the particles are under 300 microns in their longest dimension and above 5 microns in their shortest dimension.

The following examples are illustrative of the instant invention. Unless otherwise indicated, all parts are by weight and all temperatures in °C.

EXAMPLE 1

A stirred solution of 16.4 g of methomyl and 40.0 g (Du Pont) Elvacite® 2010 poly(methylmethacrylate) in 100 ml of methylene chloride was treated dropwise with 92 ml of hexane. The stirred solution was added dropwise over a 10 minute period to a solution of 10 g of Emcol® 14 (Witco Chemical Company) surfactant in 500 ml of hexane at −20° and agitated at high speed (>1,000 rpm) in a high shear Waring blender. The solid particles formed were allowed to settle, the liquid phase was decanted, and the resultant solid was agitated under high shear with 300 ml hexane at 0°, removing the methylene chloride and hardening the particles. The particulate solid, all of which passed through a 60 mesh USS screen (approx. 250μ mesh opening) was successively filtered off, dried on a suction funnel, washed with 1 liter of water containing a trace of sodium lauryl sulfate detergent, and dried in an air stream. The product contained about 20% methomyl determined by infrared analysis.

EXAMPLE 2

The process of Example 1 was carried out using high molecular weight Elvacite® 2041 poly(methylmethacrylate). The product contained 21% methomyl and was not quite as fine as that of Example 1.

EXAMPLE 3

The process of Example 1 was carried out using a solution of 2.0 g of Cab-O-Sil® silica (Cabot Corporation), 8.0 g Elvacite® 2010 and 4.1 g methomyl in 100 ml of methylene chloride. The particulate product contained approximately 20% methomyl.

EXAMPLE 4

The process of Example 1 was carried out using polystyrene (Shell 314 - Natural) as the polymer. The product contained 18% methomyl.

EXAMPLE 5

The process of Example 1 was carried out using poly(ethylmethylacrylate) (Elvacite® 2042) as the polymer. The product contained 17% methomyl.

EXAMPLE 6

The process of Example 1 was carried out using a solution of 10.0 g of poly(vinyl acetate) (Polysciences Company) and 3.75 g methomyl in 100 ml of methylene chloride into which was stirred 5.0 g Cab-O-Sil® synthetic silica. The product contained 11% methomyl.

EXAMPLE 7

The process of Example 1 was carried out using 5.0 g of poly(methylmethacrylate) (Elvacite® 2010), 5.0 g polystyrene (Shell 314-Natural) and 4.1 g of methomyl in a solution of 100 ml of methylenechloride and 50 ml of hexane. Emcol® 14 (5 g) was used in the cold hexane phase. The product contained 22% methomyl.

EXAMPLE 8

The process of Example 1 was carried out using 10.0 g Elvacite 2010 and 15.0 g methomyl in a solution of 100 m of methylene chloride and 50 ml of hexane. The product containing about 30% methomyl was successively extracted with water, two 250 ml portions, extracted similarly again after 10 weeks and again after a total of 22 weeks of aging under ambient conditions. The final extraction removed less then 0.01 g methomyl. Air drying was used after each washing. The final methomyl concentration was 20%.

EXAMPLE 9

The process of Example 1 was carried out using ethyl cellulose as polymer (Ethocel ®, Dow Chemical Company) in 125 ml methylene chloride. The product contained 17% methomyl.

EXAMPLE 10

The process of Example 1 was carried out using 4.0 g methomyl and 4.0 g Elvacite 2010 in 15 ml acetone as solvent. 200 ml $H_2O$ at 1° was used as the non-solvent. The product contained 18% methomyl.

Utility

The particulate products of this invention are useful as insecticides, applied as a dust or water-dispersible powder. They are particularly useful for control of insects in cotton.

The cotton plant has many insect pests, each of which contributes to decreasing the yield of seed cotton that can be harvested. Some insects like aphids and plant bugs feed on the sap and retard plant growth. Others like the cotton leaf perforator, beet armyworm and looper feed on the foliage and reduce the number of bolls that the plant can produce or mature. Still others, like budworms and bollworms, feed on the fruiting body late in the growing season and directly reduce or destroy the harvest. These latter pests are considered by many to be among the worst insect pests.

Methomyl provides excellent control of a great many insect pests and is particularly effective on the budworm/bollworm complex. When applied directly to cotton, however, some of it is taken up by the cotton leaves and degraded, causing the leaves to redden. Under certain growing conditions, even moderate rates of application of methomyl to most cotton varieties result in a reddening effect. Reddening is even more likely to occur at high application rates and intensive spray schedules. Growers generally prefer their cotton to exhibit a dark-green appearance.

Another problem faced by growers is the lack of residual activity of methomyl. In a few days, methomyl applied at recommended rates may lose its effectiveness. This is both inconvenient and uneconomical.

The particles produced by the process of this invention greatly retard absorption of methomyl by plant foliage, yet provide a ready source to the insect cuticle or stomach. This is indicated by the high contact activity of the particles. Cotton plants are protected from insect damage but have only a minimal opportunity to absorp methomyl. Reduced plant uptake leads to reduced degradation of methomyl and to protection from reddening of the cotton plants.

Additionally, when the particles produced by the claimed process are used, the methomyl remains available on the plant for insect control for a significantly longer period of time than when conventional formulations are used.

Use of these particles thus leads to improved insect control, reduced cotton reddening and improved residual insecticidal action when compared to conventional formulations. This means that less methomyl is required to achieve a given level of insect control resulting in increased savings and reduced dispersal of insecticide into the biosphere.

The particles described herein readily control pestiferous insects belonging to such orders as Lepidoptera, Homoptera, Hemiptera, Diptera and Coleoptera. More specifically, insects controlled by compositions of this invention include but are limited to: cotton bollworm (*Heliothis zea*), tobacco budworm (*Heliothis virescens*), southern armyworm (*Spodoptera eridania*), soybean looper (*Pseudoplusia includens*), beet armyworm (*Spodoptera exigua*), cotton aphid (*Aphis gossypii*), tarnished plant bug (*Lygus lineolaris*), and white flies (*Trialeurodes* spp. and *Bemisia tabaci*).

The insects are controlled by applying the particles in any convenient formulation to the locus of infestation, to the area to be protected, or to the pests themselves. For the control of insects in agricultural crops, the particle is generally applied to the foliage or other plant parts that are infested or which are to be protected. Effective amounts to be applied depend on the species to be controlled, its life stage, its size and location, the amount of rainfall, the time of year, moisture, temperature, type of application, and other variables. In general, 0.0625 to 4 kg/ha of the active ingredient may be required for insect control in agriculture with rates of 0.125 to 2 kg/ha usually being sufficient. Preferred rates for controlling pests in cotton are in the range of 0.125 to 1 kg/ha.

The particles may be used as is or may be formulated in conventional ways as dusts, wettable powders, or the like. They may be admixed with diluents and/or surfactants. Suitable diluents are mineral carriers such as clays, talcs, pyrophyllites, hydrous aluminosilicates, fine silicas etc., and organic carriers like finely divided wood or shell flours. Surfactants such as wetting agents, dispersing agents, antifoam agents and the like may be used along or in combination, especially if application from an aqueous spray is intended.

Application of the pesticides to plants may be made dry or by spraying from an oil or water carrier. It is often desirable to use surfactants in the oil or water carrier to improve dispersion and wetting, and such surfactants can be added into the formulation or tank-mixed into the spray. Concentrated aqueous dispersions, containing up to 20% of the powders in the spray, or dilute dispersions containing as little as 80 ppm of powder, may be used.

The insecticidal particles can be mixed with fungicides, bactericides, acaricides, nematicides, insecticides, or other biologically active compounds in order to achieve desired results with a minimum expenditure of time, effort and material. Amounts of these biologically active materials added for each part by weight of the compound of this invention may vary from about 0.05 to 25 parts by weight. Suitable agents of this type are well known to those skilled in the art. Some are listed below:

Fungicides methyl 2-benzimidazolecarbamate
tetramethyl thiuram disulfide (thiuram)
n-dodecylguanidine acetate (dodine)
manganese ethylenebisdithiocarbamate (maneb)
1,4-dichloro-2,5-dimethoxybenzene (chloroneb)
methyl 1-(butylcarbamoyl)-2-benzimidazolecarbamate (benomyl)
N-trichloromethylthiotetrahydrophthalimide (captan)
N-trichloromethylthiophthalimide (folpet)

Bactericides

Tribasic copper sulfate
streptomycin sulfate

Acaricides 3,3-dimethyl acrylic acid, ester with 2-sec-butyl-4,6-dinitrophenol (Morocide ®)
6-methyl-1,3-dithiolo[2,3-β]quinonoline-2-one (Morestan ®)
ethyl 4,4'-dichlorobenzilate (Chlorobenzilate ®)
1,1-bis(p-chlorophenyl)-2,2,2-trichloroethane (Kelthane ®)
bis(pentachloro-2,4-cyclopentadien-1-yl) (Pentac ®)
tricyclohexyltin hydroxide (Plictran ®)

Nematicides

S-methyl 1-(dimethylcarbamoyl)-N-(methylcarbamoyloxy)thioformimidate (Vydate ®)
S-methyl 1-carbamoyl-N-(methylcarbamoyloxy)thioformimidate
N-isopropylphosphoramidic acid, O-ethyl-O'-[4-(methylthio)-m-tolyl]diester (Nemacur ®)

Insecticides 3-hydroxy-N-methylcrotonamide(dimethylphosphate) ester (Azodrin ®)
methylcarbamic acid, ester with 2,3-dihydro-2,2-dimethyl-7-benzofuranol (Furadan ®)
O-[2,4,5-trichloro-α-(chloromethyl)benzyl]phosphoric acid, O',O'-dimethyl ester (Gardona ®)
2-mercaptosuccinic acid, diethyl ester, S-ester with thionophosphoric acid, dimethyl ester (Malathion ®)
phosphorothioic acid, O,O-dimethyl, O-p-nitrophenyl ester (methyl parathion)
methylcarbamic acid, ester with α-naphthol (Sevin ®)
methyl O-(methylcarbamoyl)thiolacetohydroxamate (methomyl)
N'-(4-chloro-o-tolyl)-N,N-dimethylformamidine (Galecron ®)
O,O-diethyl-O-(2-isopropyl-4-methyl-6-pyrimidyl-phosphorothioate (Diazinon ®)
octachlorocamphene (toxaphene)
O-ethyl O-p-nitrophenyl phenylphosphonothioate (EPN)
cyano(3-phenoxyphenyl)-methyl-4-chloro-α-(1-methylethyl)benzeneacetate (Pydrin ®)
(3-phenoxyphenyl)methyl(±)-cis,trans-3-(2,2-dichloroethenyl)-2,2-dimethylcyclopropanecarboxylate (Ambush ®)
O-ethyl-S-(p-chlorophenyl)ethylphosphonodithioate (Curacron ®)
phosphorothiolothionic acid, O-ethyl-O-[4-(methylthio)phenyl]-S-n-propyl ester (Bolstar ®)

EXPERIMENT I

The foliage of Red Kidney bean plants in the two-leaf stage (~8 days from planting) is sprayed to run-off with dispersions of the preparations listed below. Dispersions are prepared by stirring appropriately weighed quantities of the powders in water containing sodium lauryl sulfate at 1:5000 and further diluting to 100 ml. After drying, leaves are excised and placed in covered 10-cm Petri dishes along with moist filter paper to keep them turgid. Ten southern armyworm larvae are placed in each dish. The test units are kept in a room maintained at 77°±2° F. and 55±5% R.H. Results are recorded at the end of two days and are listed below.

| Treatment | Active Ingredient Spray Concentration (ppm) | % Mortality (2 Days) |
|---|---|---|
| Methomyl (Control) | 100 | 5 |
| Product of Example 1 | 100 | 100 |
| Untreated | — | 0 |

EXPERIMENT II

Fifty ml portions of dispersions of the test material prepared by the procedure described in Example 1 are poured over 10 southern armyworm larvae placed in a Buchner funnel (8 cm in diameter). The larvae are then transferred using forceps to Petri dishes containing moistened filter paper and an excised bean leaf for food. Results are read two days later.

| Treatment | Concentration (ppm) | % Mortality (2 Days) |
| --- | --- | --- |
| Example 1 | 100 | 100 |
| Untreated | — | 0 |

EXPERIMENT III

An experiment is performed that is similar in all respects to Experiment I except that leaves are excised from the plants and fed to southern armyworm larvae at various intervals after treatment rather than immediately. Results are evaluated two days later.

| Treatment | Active Ingredient Spray Conc. (ppm) | % Mortality (Days) | | | |
| --- | --- | --- | --- | --- | --- |
| | | 2 | 5 | 7 | 9 |
| Methomyl (Control) | 100 | 0-15 | 0 | | |
| Product of: | | | | | |
| Example 1 | 50 | 100 | 90 | | |
| | 100 | 100 | — | 93 | 90 |
| Example 2 | 100 | 100 | 95 | — | — |
| Example 3 | 100 | 90 | — | — | — |
| Example 4 | 100 | 90 | — | — | — |
| Example 5 | 100 | 100 | — | — | — |
| Example 6 | 100 | 70 | — | — | — |
| Example 7 | 100 | 100 | — | — | — |
| Example 8 | 100 | 100 | — | 100 | — |
| | 50 | 100 | — | 100 | |
| Example 9 | 100 | 80 | — | | |
| Example 10 | 100 | 100 | | | |
| Untreated | — | 0 | — | — | — |

EXPERIMENT IV

An experiment is performed that is similar in all respects to that described in Experiment I except that the excised leaves are fed to soybean loopers. Excellent control is obtained.

| Treatment | Active Ingredient Spray Conc. (ppm) | % Mortality (2 Days) |
| --- | --- | --- |
| Product of Example 1 | 400 | 100 |
| | 200 | 100 |
| | 100 | 80 |

EXPERIMENT V

Potted cotton plants approximately 25 cm high having 3-4 true leaves are sprayed to run-off with aqueous dispersions of compositions of this invention at 500 ppm. The sprays contain sodium lauryl sulfate at a concentration of 1:5000. Another set of plants is similarly treated with methomyl. After drying, plants are set out in the greenhouse and held for observation.

| Treatment (500 ppm AI)[1] | Rating[2] | |
| --- | --- | --- |
| | 7 Days | 8 Days |
| Product of: | | |
| Example 1 | trace R | — |
| Example 2 | trace R | — |
| Example 3 | 2R | — |
| Example 4 | 0.5R | — |
| Example 5 | — | 0.2R |
| Example 6 | — | 0.2R |
| Methomyl Control | 3R | — |
| Untreated | 0 | — |

[1] AI = active ingredient.
[2] R denotes typical methomyl effect, i.e., reddening of older leaves, slight puckering and black stippling of younger leaves. Rating is on the basis of 0-10, with 10 indicating total leaf area involvement.

What is claimed is:

1. A process for preparing controlled release particles of methomyl which comprises:
    (a) dissolving a water-insoluble polymer and methomyl in an organic solvent, the concentration of methomyl in the resulting solution being about 1-50% by weight and the concentration of said polymer in the resulting solution being about 1-60% by weight;
    (b) comingling, with high shear agitation, said methomylpolymer solution with a nonsolvent for both methomyl and said polymer, to produce particles of polymer embedded with methomyl;
    (c) and recovering said particles; wherein
        (i) said organic sovlent is miscible with said nonsolvent, and
        (ii) said polymer is poly(methylmethacrylate), poly(ethylmethacrylate), methylmethacrylate or ethylmethacrylate or styrene copolymers with polar monomers, ethyl cellulose, cellulose acetate, cellulose acetatebutyrate, polystyrene, polyvinyl chloride or vinyl chloride-vinyl acetate copolymers.

2. The process of claim 1 wherein the polymer is poly(methylmethacrylate).

3. The process of claim 1 wherein the solvent is a halogenated aliphatic.

4. The process of claim 1 wherein the nonsolvent is an alkane of five to eight carbon atoms.

5. The process of claim 1 wherein the polymer is poly(methylmethacrylate), the solvent is methylene chloride, and the non-solvent is hexane.

6. The process of claim 1 where the polymer is poly(methylmethacrylate), the solvent is acetone and the non-solvent is water.

7. The process of claim 1 wherein the particles are washed with non-solvent and water prior to recovery.

* * * * *